United States Patent [19]
Huey et al.

[11] Patent Number: 6,104,941
[45] Date of Patent: Aug. 15, 2000

[54] PHYSIOLOGICAL SENSOR

[75] Inventors: Raymond J. Huey; Gary A. Jordan; Simon W. H. Thomas; Robert J. Graumann, all of Wallingford, Conn.

[73] Assignee: GE Marquette Medical Systems, Inc., Milwaukee, Wis.

[21] Appl. No.: 09/048,689

[22] Filed: Mar. 26, 1998

[51] Int. Cl.$^7$ ............................................. A61B 5/04
[52] U.S. Cl. ...................... 600/376; 600/338; 600/339; 604/99
[58] Field of Search ............. 604/97–100; 600/373–376, 600/313, 338, 351

[56] References Cited

U.S. PATENT DOCUMENTS

| | | | |
|---|---|---|---|
| 4,156,422 | 5/1979 | Hildebrandt et al. | 128/748 |
| 4,159,722 | 7/1979 | Walker | 137/496 |
| 4,270,541 | 6/1981 | Okamoto et al. | 128/344 |
| 4,332,254 | 6/1982 | Lundquist | 128/344 |
| 4,338,943 | 7/1982 | Okamoto et al. | 128/344 |
| 4,543,965 | 10/1985 | Pack et al. | 128/748 |
| 4,794,910 | 1/1989 | Mushika | 600/18 |
| 4,938,218 | 7/1990 | Goodman et al. | 128/633 |
| 5,087,244 | 2/1992 | Wolinsky et al. | 604/53 |
| 5,109,849 | 5/1992 | Goodman et al. | 128/633 |
| 5,222,485 | 6/1993 | Jerath | 128/660.01 |
| 5,247,932 | 9/1993 | Chung et al. | 128/633 |
| 5,300,027 | 4/1994 | Foote et al. | 604/100 |
| 5,377,675 | 1/1995 | Ruskewicz et al. | 128/634 |
| 5,460,609 | 10/1995 | O'Donnell | 604/100 |
| 5,746,212 | 5/1998 | Rall et al. | 600/483 |
| 5,916,155 | 1/1999 | Levinson et al. | 600/338 |

FOREIGN PATENT DOCUMENTS

WO 91/07910 6/1991 United Kingdom .

*Primary Examiner*—Linda C. M. Dvorak
*Assistant Examiner*—David M Ruddy
*Attorney, Agent, or Firm*—Michael Best & Friedrich; Christian G. Cabou; Phyllis Y. Price

[57] ABSTRACT

The combination of a pressure control and a catheter including an elongate member, a sensor mounted on the catheter and adapted to be placed in pressure engagement with tissue for sensing signals resulting from physiological phenomena and an expandable member mounted on the elongate member for maintaining the sensor in contact with the tissue. A pressure source is connected to the expandable member for maintaining the expandable member inflated and a pressure controller coupled to the expandable member for maintaining the contact pressure between the sensor and the tissue within preselected limits.

15 Claims, 6 Drawing Sheets

PHYSIOLOGICAL SENSOR

BACKGROUND OF THE INVENTION

This invention relates to catheters used for detecting physiologic signals or used for therapeutic functions.

Many catheters used to detect physiological signals must be maintained in intimate contact with a physiologic member or tissue section in order to accurately and reliably detect a signal to measure a physiological parameter or deliver a therapy from or through the surface of the skin, mucosal membrane or vessel wall. Such catheters may, for example, include INTRA UTERINE CATHETERS, pulse oximetry sensors, ECG sensors, temperature or blood pressure sensors, used for measuring ECGs, oxygen tension, pH, oxygen saturation, biochemical analysis of skin and/or skin secretions, surface or skin temperature, blood pressure and the like.

Such devices generally include a sensing element and a mechanism for holding the element in pressure engagement with the member or tissue. When such sensors are held in position there is a possibility of tissue damage, patient discomfort or undesirable physiological reflex response to the applied pressure which may cause damage to surrounding or underlying tissue, measurement artifact and/or a reduction in quality of the signal acquired from the skin or tissue surface. For example, in reflection pulse oximetry, excessive sensor pressure can cause local exsanguination of blood from the underlying tissue structure, changing the optical absorption characteristics and thus introducing errors into the oxygen saturation calculated from the optical signals detected after transmission through the tissue section. Similarly, a sensor mounted on a rectal, fecal or esophageal catheter is required to be maintained in place without overextending the surrounding tissue and causing damage.

Another type of catheter is intended to be positioned in a body opening such as the cervix or esophagus for the delivering of a fluid or other therapy. Such catheters may also be positioned by a balloon in the uterus, at the cervical opening, for the purpose of inducing labor, delaying delivery or withdrawing amniotic fluid. Another use of balloon catheters is to block the esophagus during surgery to prevent the contents of the patient's stomach from being aspirated into the lungs. In these types of catheters, it is highly desirable to prevent excessive pressure in the balloon from overextending and possibly damaging tissue or underlying organs.

SUMMARY OF THE INVENTION

The primary object of the invention is to provide a new and improved system for maintaining a catheter's position and contact pressure in a body opening without damage to the contacted tissue, patient discomfort or undesirable reflex response and to improve the quality of signals gathered by sensing devices mounted on such a catheter.

Another object of the invention is to provide a system for positioning and maintaining both measurement sensors and catheter in a designated location without tissue damage, patient discomfort or undesirable reflex response.

A further object of the invention is to provide a system for sensing or measuring physiological signals wherein the contact pressure between a sensor and the member or tissue is maintained within predetermined limits.

It is another object of the invention to provide a system for maintaining catheter position and contact pressure within preselected limits to minimize deformation of the tissue being contacted.

A still further object of the invention is to provide a system for sensing physiological signals wherein contact pressure does not result in exsanguination of blood from the underlying tissue or damage to underlying or surrounding tissue.

Yet another object of the invention is to provide a fetal monitoring system in which the catheter component can be accommodated to a range of fetal/uterine sizes and shapes.

It is another object of the invention to provide a system for positioning a catheter within a body opening without damaging the underlying or surrounding tissue being contacted.

These and other objects and advantages of the invention will become more apparent from the detailed description thereof taken with the accompanying drawings.

In general terms, the invention comprises, the combination of a pressure control system and a catheter constructed and arranged to be positioned in a passage or cavity in a human or animal body. The catheter includes an elongate member and an expandable member mounted on the elongate member and constructed and arranged to expand and engage tissue forming the margins of the passage or cavity upon being pressurized. A pressure source is coupled to the expandable means and constructed and arranged to expand said expandable member, and a pressure control is coupled to the expandable member and constructed and arranged to maintain the pressure within said expandable member within preselected limits for maintaining the contact pressure between the expandable member and the tissue forming the passage or cavity within preselected limits to minimize the risk of tissue damage, patient discomfort or physiological reflex response.

According to another aspect, the invention comprises pressure control means coupled to contact pressure application means via a catheter constructed and arranged to be positioned in a passage in a human or animal body. The catheter includes an elongate member and an expandable means mounted on the member for extending to engage the tissue forming the passage when the expandable means is expanded. Pressure means is provided for inflating the expandable means and pressure control means as coupled to the expandable means for maintaining the pressure within the expandable means within preselected limits.

According to a more specific aspect, the invention comprises a catheter for sensing physiologic signals and includes sensing means adapted to be placed in pressure engagement with tissue for sensing signals resulting from physiological phenomena, pressure means for maintaining the sensing means in contact with the tissue, and pressure control means coupled to the pressure means for maintaining the contact pressure between the sensing means and the tissue within preselected limits to minimize the risk of tissue damage, the exsanguination of blood from beneath the sensor contact area and the introduction of errors into the sensor signal.

According to various embodiments of the invention, the sensor is constructed and arranged for sensing skin or surface temperature, ECG, oxygen saturation by pulse oximetry, pH, oxygen tension, biochemical analysis of skin or skin secretions. The catheter may be constructed and arranged to place the sensor in contact with the patient's skin, tissue or mucosal membrane and maintain proper placement during movement, uterine contractions or other circumstances likely to dislodge the sensing elements from their optimum contact position.

According to another aspect, the invention comprises a method of positioning a catheter within a body passage wherein the catheter includes an elongate member constructed and arranged to be received in the passage, and an expandable means having an outer surface movable away from the member upon expansion of the expandable means. The method includes the steps of positioning the expandable means within the passage, expanding the expandable means to move the outer surface into pressure engagement with the tissue forming the passage, and controlling the contact pressure between the surface and the tissue to prevent tissue damage, patient discomfort or undesirable physiological reflex response.

According to other embodiments, the passage comprises an esophagus or cervical entrance to the uterus and the inflatable means is constructed and arranged for engaging the esophageal or cervical/uterine tissues.

DETAILED DESCRIPTION OF THE INVENTION

Figure 1:
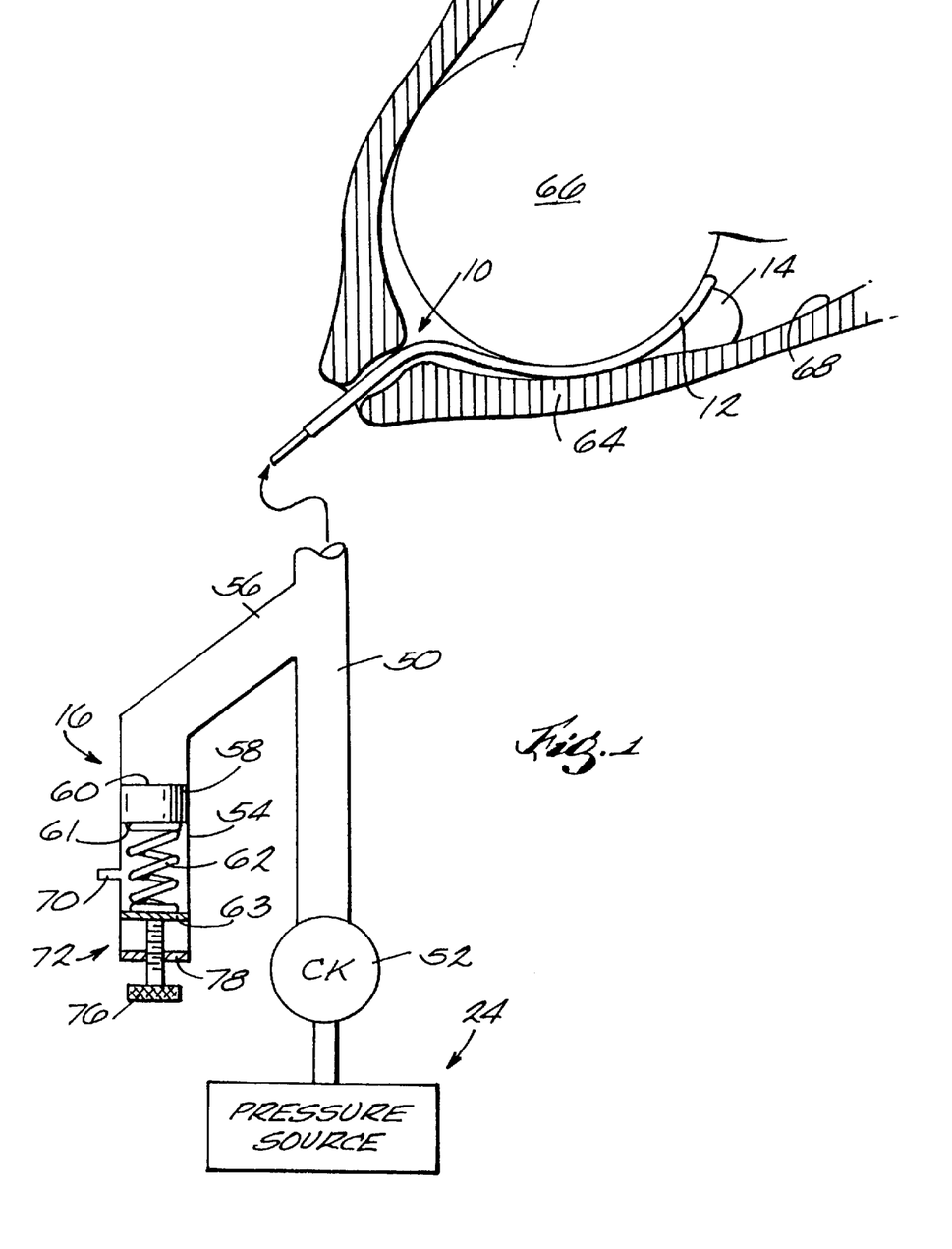
FIG. 1 schematically illustrates a first embodiment of a system for sensing physiologic signals.

FIG. 1 illustrates a first embodiment of the invention to comprise a catheter 10, sensing means or sensor 12 mounted on the catheter 10 for sensing physiological signals, an expandable means or member 14 for maintaining the sensing means 12 in contact with the tissue from which the physiological signal is being detected and a pressure control 16 or means for maintaining the pressure in the expandable means or member 14 within predetermined limits.

Figure 2:
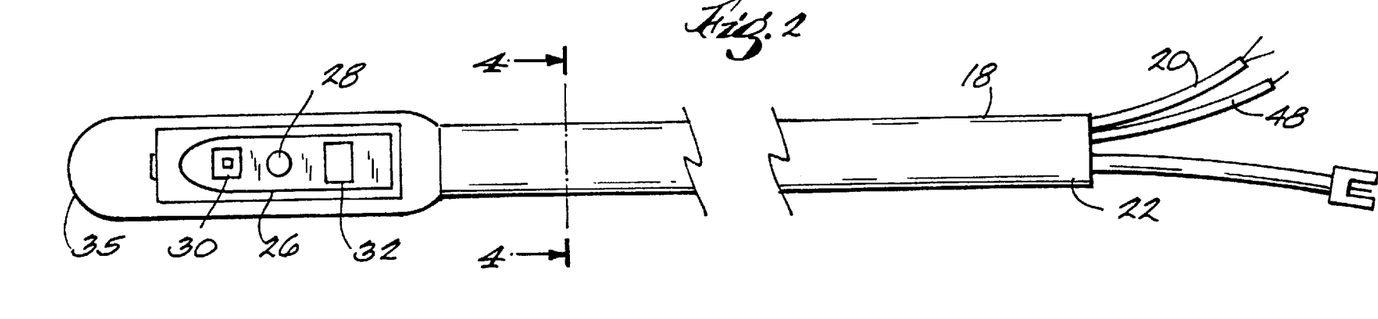
FIG. 2 is a top view of a catheter usable with the system of FIG. 1, prior to insertion, with the balloon deflated.
Figure 3:
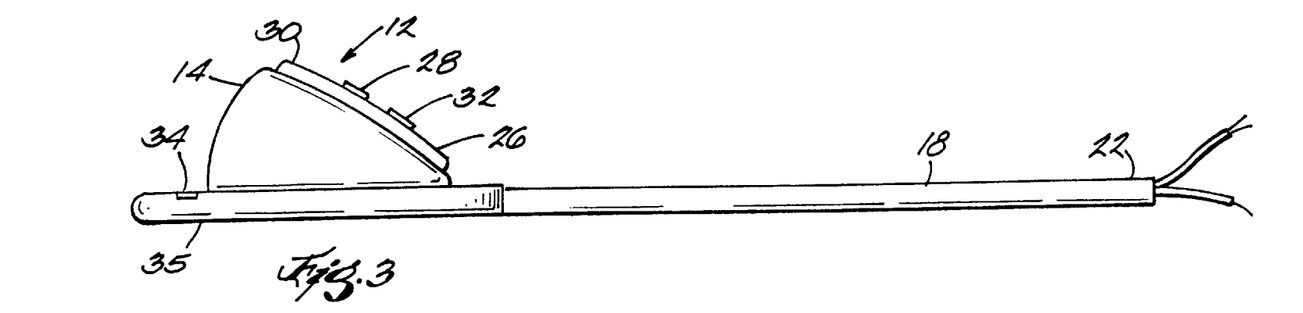
FIG. 3 is a side view of the catheter illustrated in FIG. 2, with the balloon inflated.
Figure 4:
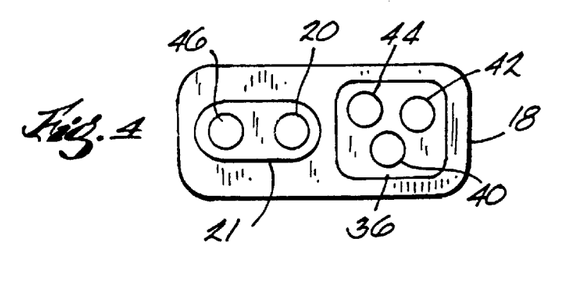
FIG. 4 is a view taken along lines 4—4 of FIG. 3.

In the embodiment of the invention illustrated in FIG. 1, the catheter 10 comprises a catheter for fetal monitoring. FIGS. 2–4 illustrate the fetal monitoring catheter 10 in greater detail. Specifically, the catheter 10 includes an elongate, generally rectangular in cross section, flexible member 18 formed of any suitable material to enable insertion.

The expandable means or expandable member 14 preferably comprises an inflatable membrane or balloon mounted adjacent the distal end of the member 18. The membrane or balloon 14 is formed of an extensible or nonextensible material such as polyurethane, rubber or like substances such as latex, a thermoplastic elastomer, or other thermoplastic material. An opening (not shown) in the member 18 permits conduit 20 to pass through an elongate lumen 21 extending axially within member 18 from the proximal end 22 connecting to the interior of the membrane or balloon 14. As will be discussed in greater detail herein below, the conduit 20 is connected to a source 24 of a pressurized fluid.

The sensor or sensing means 12 is mounted directly, or via a carrier 26 to the membrane or balloon 14. The sensing means or sensor 12 comprises one or more elements constructed and arranged for detecting or sensing the physiological functions being monitored or sensed. In the illustrated embodiment the sensing means or sensor 12 includes an ECG electrode 28 and pulse oximetry sensors consisting of two sources of illumination 30 and a light detector 32. As those skilled in the art will appreciate, the light sources 30, which may comprise LEDs, for example, projects light into the tissue at red and infrared wavelengths. The difference between the light absorbed at each wavelength is used to determine the oxygen saturation of the blood. An ECG reference electrode 34 may be mounted on the body between the sensing means or sensor 12 and the distal end 35 of the body 18.

Lumen 36 is provided for receiving conductors 40, 42 and 44 connected, respectively, to the ECG electrode 28, the oximetry light sources 30 and the photo detector 32. Lumen 21 may also permit an additional conduit 46 to pass through elongate body 18 for amniotic fluid sampling or infusion at the distal end 35 of the catheter or the insertion of other sensors or instruments.

The pressure source 24 of FIG. 1 comprises any source of fluid under pressure, and may comprise, for example, a syringe filled with liquid, such as, water or a saline solution. Pressure source 24 is connected by a conduit 50 to the membrane or balloon 14. A check valve 52 is disposed between the pressure source 24 and the conduit 50.

The pressure control 16 includes a cylinder 54 connected by a conduit 56 to the conduit 50. A piston 58 is disposed within cylinder 54 and has a first face 60 exposed to conduit 56 and an opposite face 61 which is engaged by a biasing spring 62 the opposite end of which engages an adjusting plate 63.

In operation, the fetal catheter 10, with the membrane or balloon 14 deflated, is introduced through the mother's cervix 64, passing between the presenting part of the fetus 66, which is usually the fetal head, and the opposite uterine wall 68. When the catheter has been positioned to a length of approximately fifteen centimeters, past the maximum diameter of the fetal head, the pressure source 24 is actuated to inflate the balloon 14. Slight tension is applied to the catheter 10 by the attendant to ensure that the sensor means 12 is securely held against the fetal scalp with the inflated balloon 14 wedged between the maternal tissue 68 and the fetal head 66. It will be appreciated that this wedging action maintains the position of the sensor means 12 even in the face of uterine contractions or other maternal or fetal movements.

Maternal uterine contractions or fetal movements compress the balloon 14, thereby increasing the pressure between the sensor means 12 and the fetal scalp. This raises the possibility of damaging the fetal tissue, eliciting an undesirable physiological reflex response or causing the exsanguination of blood from beneath the oximetry sensors being maintained in contact by the wedging action of the balloon 14, thereby adversely affecting the oximetry measurement. Moreover, pressure variations at the measurement site can produce baseline drift of the fetal ECG signal, thereby adversely affecting fetal heart-rate signal quality. These deficiencies are alleviated by the pressure control means 16. As the pressure on the balloon 14 increases during initial inflation, a uterine contraction or fetal movement, the pressure within the conduit 56 increases, thereby forcing the piston 58 downwardly within the cylinder 54 to permit a quantity of liquid to flow from the interior of the balloon 14 into the upper end of the cylinder 54. As the uterine contraction ceases, so that the pressure applied to the balloon 14 decreases, the force exerted by the spring 62 on the piston 58 becomes greater than the back pressure of the liquid in conduit 56. As a result, the piston moves upwardly within the cylinder 54 until the pressure within the balloon 14 returns to a preselected normal value. A bleed tube 70 is connected intermediate at the ends of the cylinder 54 to permit fluid to be bled from the system should the pressure within the cylinder 54 exceed a predetermined maximum limit. During inflation of the balloon 14, the spring-biased piston 58 also serves to limit the maximum applied pressure applied from the pressure source 24. An indicator 71 may also be provided to show when the optimum application pressure has been achieved during placement of the catheter.

The pressure exerted by the biasing spring 62 may be adjusted by an adjusting mechanism 72 consisting of the plate 63 which is engaged by one end of the spring 62 and an adjusting screw 74 which passes through a threaded opening 78 in the lower end of the cylinder 54 and whose end abuts the plate 74.

Figures 5, 6:
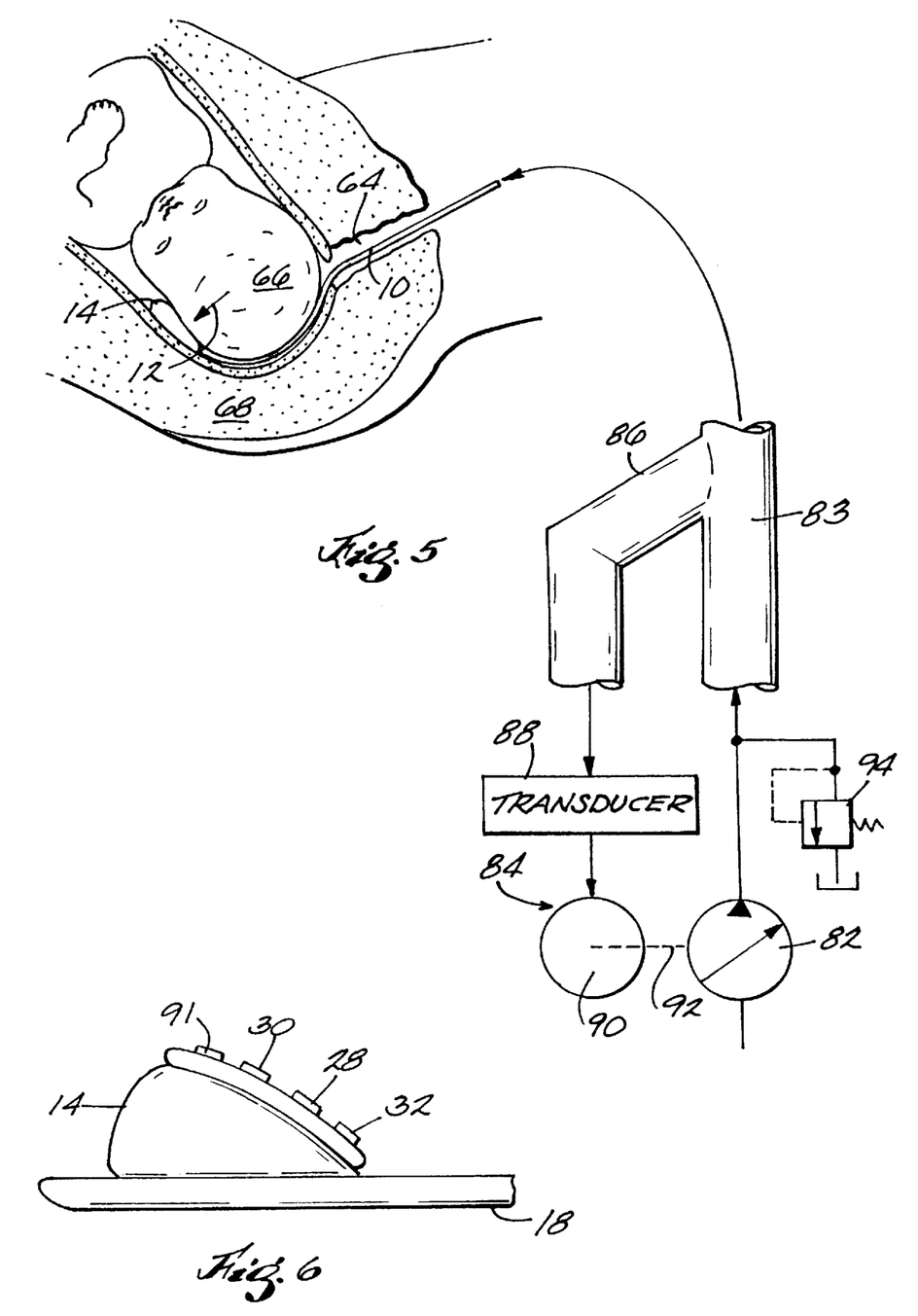
FIG. 5 schematically illustrates an alternate embodiment of the invention.
FIG. 6 schematically illustrates a further embodiment of the invention.

FIG. 5 shows an alternate embodiment of the invention to include an adjustable pressure source 82 connected to the balloon 14 by a conduit 83. A pressure control means 84 is connected to conduit 83 by conduit 86 for sensing the pressure within balloon 14. The pressure control means 84 is also coupled to the adjustable pressure source 82 to control the output of the pressure source 82 to maintain the pressure within the balloon 14 within predetermined limits. The pressure source 82 may be any conventional pressure source that can be regulated, such as, a variable displacement pump. The pressure control means may include, for example, a transducer 88 which converts the pressure within conduit 86 into an electrical signal and a servo-motor 90 coupled to the transducer 88 for receiving the output signal therefrom. Alternatively, a pressure sensor 91 may be mounted directly onto the expandable means 14 contacting the tissue providing an electrical signal to the servo-motor directly related to the contact pressure as shown in FIG. 6. The servo-motor 90 is operative to position its output shaft 92 coupled to the pump 82, in accordance with the signal from transducer 88 or the pressure sensor 91. In this manner, the pressure delivered from pump 82 is maintained within predetermined limits. A pressure relief valve 94 may be coupled to the conduit 83 to prevent overpressure within balloon 14. An indicator 71 as shown in FIG. 1 may be provided to show when the optimum application pressure has been achieved during placement of the catheter.

FIG. 7 shows a catheter 100 used for measuring a physiologic signal from a mucosal membrane, such as the patient's esophagus 102. The catheter 100 includes a sensor 104 which may, for example, comprise an ECG electrode, a pulse oximetry sensor, a temperature sensitive device, or the like. The catheter 100 is located in the desired position within the esophagus; the balloon 106 is inflated through a conduit, located with a lumen (not shown) within catheter 100. As the balloon 100 expands, the sensor is forced against the mucosal membrane. An indicator 71 may be provided to show when the optimum application pressure has been achieved during placement of the catheter.

Figure 8:
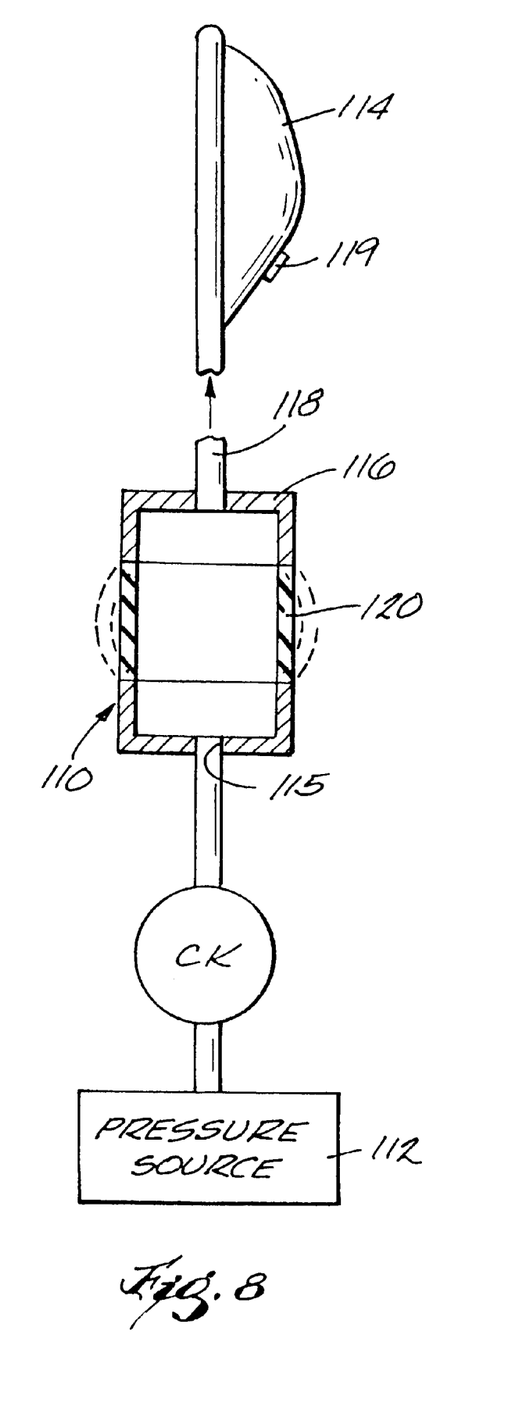

FIG. 8 shows yet another alternative embodiment of the invention, which includes a fluid filled reservoir 110, located either between the pressure source 112 and the balloon 114 or at the end of a separate branch conduit (not shown). The reservoir consists of a cylinder with openings 115 and 116 at either end, connected in-line with the filling conduit 118. A section 120 of the cylinder is formed from a resilient material and the remaining portions are relatively rigid. After filling the balloon 114 from the pressure source 112, excess pressure inside the balloon causes fluid to flow back through the filling conduit 118 into the reservoir 110, deflecting the elastic side wall portion 120. As the pressure on the balloon 114 relaxes, the elasticity of the side wall portion 120 forces fluid back down the filling conduit 118 to re-inflate the balloon 114 thereby maintaining the sensors 119 in contact with the tissue. During balloon inflation, the elastic wall portion 120 also serves to limit the maximum applied pressure applied from the pressure source. An indicator such as 71 shown in FIG. 1, may be provided to show when the optimum application pressure has been achieved during placement of the catheter.

Figure 9:
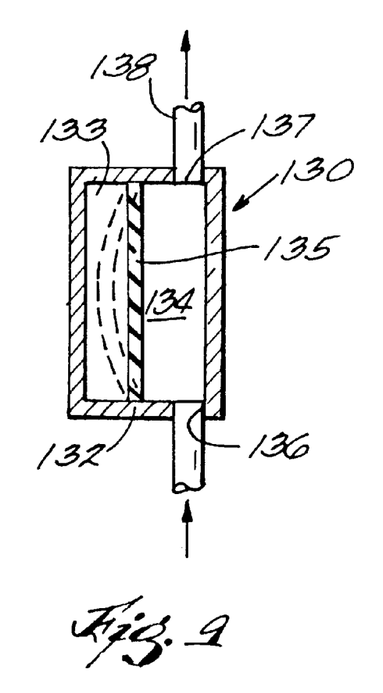
FIGS. 9–11 schematically illustrates further embodiments of the invention.

FIG. 9 shows an alternative embodiment of the invention to include a fluid reservoir 130 in place of the reservoir 110 of FIG. 8 connected either in-line with the balloon or at the end of a branch conduit (not shown). Reservoir 130 consists of a solid-walled chamber 132, one side 133 of which may be vented to atmosphere, with the side 134 closed by an elastic diaphragm or membrane 135. End openings 136 and 137 are connected, respectively, to the pressure source (not shown) and the balloon (not shown). After filling the balloon from the pressure source, excess pressure inside the balloon causes fluid to flow back through the filling conduit 138 into the reservoir 130, deflecting the elastic membrane 135. As the pressure on the balloon relaxes, the elasticity of this membrane 135 forces fluid back down the filling conduit 136 to re-inflate the balloon thereby maintaining the sensors in contact with the tissue. During balloon inflation, the elastic membrane also serves to limit the maximum applied pressure applied from the pressure source. An indicator, such as that shown in FIG. 1, may be provided to show when the optimum application pressure has been achieved during placement of the catheter.

In addition to positioning the catheter within a body passage for the purpose of maintaining a sensor or electrode in contact with the patient's tissue, the invention also contemplates positioning the catheter in a body passage for the purpose of occluding the passage, delivering medication, sampling fluids, or for other therapeutic purposes.

Figure 10:
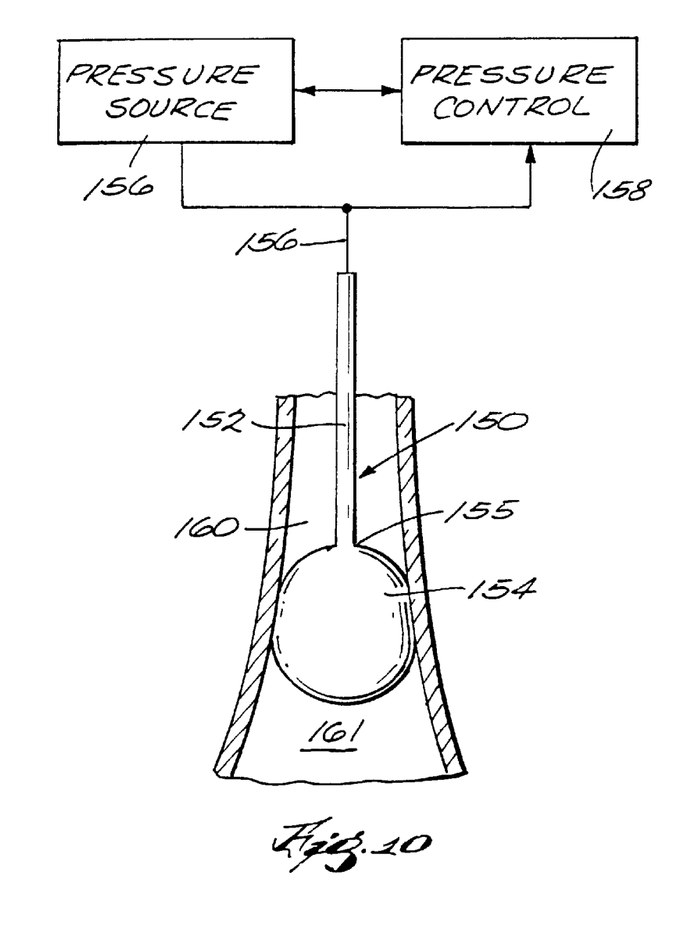

FIG. 10 shows a further embodiment of the invention to comprise a catheter 150 consisting of an elongate member 152 and an expandable member 154 at its distal end 155. A lumen (not shown) extends longitudinally within the member 152 and permits the connection of a conduit 156 between the expandable member 154 and a fluid pressure source 156. Pressure control means 158 is connected to the pressure source and to the conduit within member 152 for sensing the pressure within the expandable member 154 and for controlling the output of the pressure source to maintain the pressure within expandable member 154 within predetermined limits.

The catheter 150 is employed to prevent the contents of a patient's stomach from being aspirated into the lungs during surgery. In operation, the catheter 152 is positioned in the esophagus 160 with the expandable member 154 at the junction between the esophagus 160 and the stomach 161. Expandable member 154 is then inflated to occlude this opening and prevent the egress of the contents of the patient's stomach.

As the member 154 is inflated, its outer surface presses against the mucosal membrane of the esophagus 160. The pressure within the member 154 is sensed by the control 158. Insufficient pressure may result in separation between the member 154 and the esophageal tissue while overpressure may result in damage to the patient's diaphragm. The control 158 maintains the pressure from source 156 within a preselected range to prevent over or under pressure. The expandable member 154 is preferably a balloon.

Figure 11:
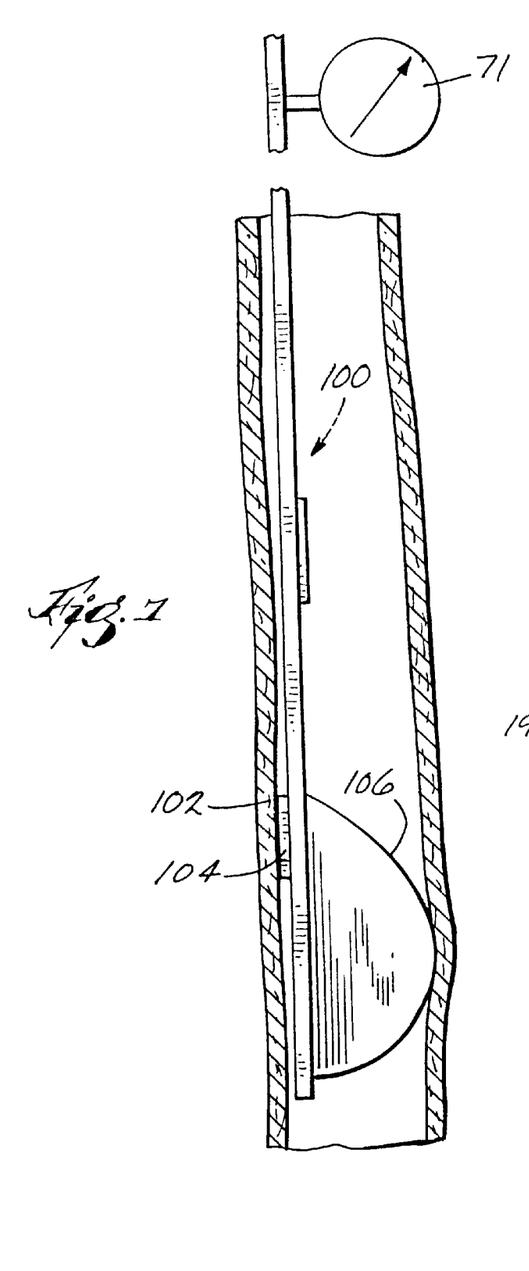

FIG. 11 shows an alternate embodiment of the invention wherein the passage comprises the cervix and uterus 162 of a pregnant woman. The catheter 163 includes an elongate member 164, a first expandable member 166 adjacent its distal end 167 and a second expandable member 168 spaced from the distal end 167. The catheter 163 is positioned through the cervix 162 so that the first expandable member 166 is at the opening of the uterine cavity 170 and the second expandable member 168 is positioned within the neck of the cervix 160. A first conduit 172 extending through a lumen in member 164 (not shown) is connected at one end to the first expandable member 166 and a second conduit 174 is connected at one end to the second expandable member 168. The other ends of conduits 172 and 174 are connected to a pressure source 176 for pressurization. Each of the conduits 172 and 174 are also connected to a pressure control 178 which, in turn, is connected to the pressure source 176. In operation, the catheter 163 is positioned in the cervix 162 so that the expandable member 168 is positioned in the cervix and the expandable member 166 is positioned in the opening to the uterine cavity 180. The pressure source 176 is then actuated to expand the expandable members 166 and 168 which are expanded with their outer surfaces moving into pressure engagement with the cervical tissue. The pressure control 178 regulates the pressure source 176 so that the pressure exerted by the expandable members 166 and 168 are sufficient to occlude the opening of the cervix but do not create pressure which will result in damage to the cervical tissue, to the amniotic membrane 180 or the fetus (not shown). The lumen in elongate member 164 (not shown) may contain additional conduits 182 and 184 for delivering medication to the amniotic sac, to the uterus, to the fetus or for sampling amniotic fluids. These medications may be provided for therapeutic purposes or to induce or retard labor and/or retard or prevent delivery.

Figure 12:
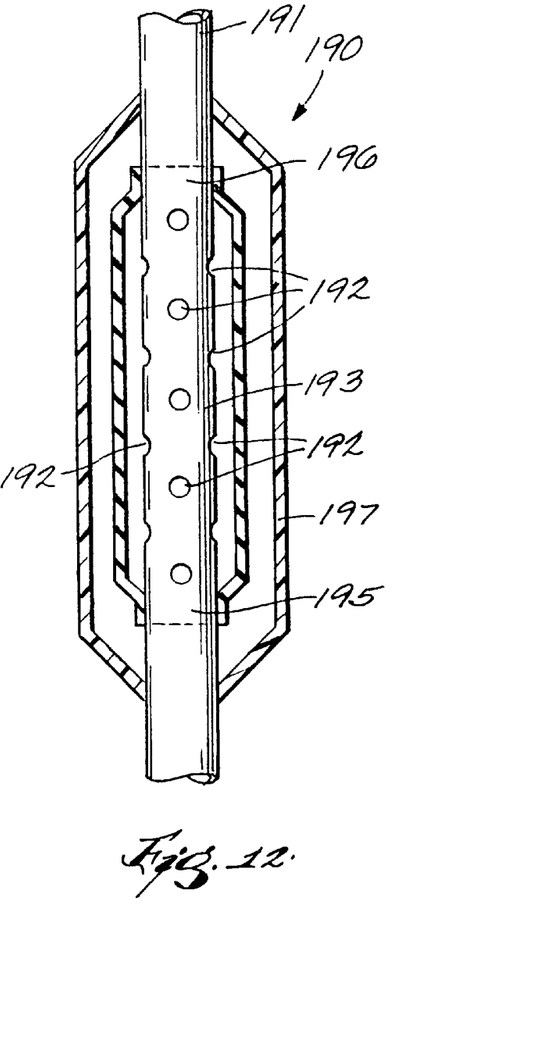
FIG. 12 illustrates a further embodiment of the invention.

FIG. 12 shows an alternate embodiment of the invention to comprise a catheter 190 consisting of an elongate member 191 having an expandable member (not shown) at its distal end. A lumen (not shown) in member 190 connects the expandable member to a pressure source (not shown) through a check valve (not shown) in a manner similar to that illustrated in FIG. 8. A plurality of openings 192 are formed in a short section 193 of the member 191. A fluid impervious expandable membrane 194 surrounds the section 192 and is sealed at its opposite ends 195 and 196 to the member 191. The membrane 194 may be formed of any suitable material, such as, rubber, polyurathane and the like which expands under pressure and is fluid impervious. A plastic housing 197 may be fixed to the member 191 in surrounding relation to the membrane 194.

Operation of the embodiment of FIG. 12 is similar to that of FIG. 8. In particular, as the pressure in the balloon (not shown) increases above a desired value, back pressure within member 191 causes fluid to flow outwardly through openings 192 and into membrane 194 causing the membrane to expand. Upon a reduction in pressure within the balloon, fluid from within membrane 194 flows back through openings 192 to the member 191. The membrane 194 thus acts as a pressure control for maintaining the pressure between the balloon and the patient's tissue.

FIGS. 1, 5, 7, 8, 9, 10, 11 and 12 show various embodiments of the invention employed in different applications. This is not intended to be limiting since several of the embodiments may be employed in various applications.

While only a few of the embodiments of the invention have been illustrated and described, it is not intended to be limited thereby, but only by the scope of the intended claims.

We claim:

1. The combination of a pressure control system and a catheter constructed and arranged to be positioned in a passage or cavity in a human or animal body, said combination including an elongate member, expandable means mounted on the member for expanding to engage tissue forming the margins of the passage or cavity upon being pressurized, pressure supply means coupled to the expandable means for expanding said expandable means, and means coupled to the expandable means for maintaining the pressure within said expandable means within preselected limits for indicating, maintaining and/or controlling the contact pressure between the expandable means and the tissue forming the passage or cavity within preselected limits to minimize the risk of tissue damage, patient discomfort or physiological reflex response, said means for maintaining pressure including an elastic diaphragm coupled to said pressure source and to said expandable means, the elastic member operable to expand to permit the flow of fluid from the expandable means when the applied pressure on the expandable means increases regardless of the speed of the pressure increase and to contract to return fluid to the expandable means when the applied pressure decreases.

2. The combination set forth in claim 1 further comprising:

sensing means adapted to be placed in pressure engagement with tissue for sensing physiological signals resulting from physiological phenomena, said expandable means being constructed and arranged for maintaining the sensing means in pressure engagement with the tissue, said means for maintaining pressure being coupled to the expandable means for maintaining the contact pressure between the sensing means and the tissue within preselected limits to minimize the risk of tissue damage, patient discomfort, physiological reflex response, the exsanguination of blood from beneath the sensor contact area or a likelihood of an introduction of errors into the signal acquired by the sensors.

3. The combination set forth in claim 2 wherein said catheter comprises a fetal monitoring catheter, said expandable means being shaped to be wedged between the fetal head and the uterine wall of the mother from which pressure is applied to the inflatable means as a result of maternal uterine contractions.

4. The combination set forth in claim 2 wherein said sensing means comprises a contact ECG electrode.

5. The combination set forth in claim 2 wherein said sensing means comprises a blood pressure sensor.

6. The combination set forth in claim 2 wherein said sensing means comprises a temperature sensor.

7. The combination on set forth in claim 2 wherein said sensing means is a pulse oximetry sensor means including light sources and a light detector.

8. The combination set forth in claim 2 wherein the tissue is a mucosal membrane said sensing means comprising an ECG electrode.

9. The catheter set forth in claim 2 wherein the tissue is a mucosal membrane said sensing means comprising a pulse oximetry sensor means including light sources and a light detector.

10. The combination of a closed-circuit pressure control system and a catheter constructed and arranged to be positioned in a passage or cavity in a human or animal body, said catheter including an elongate member, and an expandable member mounted on the elongate member and constructed and arranged to expand and engage tissue forming the margins of the passage or cavity upon being pressurized, said pressure control system including a pressure source coupled to the expandable member and constructed and arranged to expand said expandable member, and a pressure control coupled to the expandable member and constructed and arranged to maintain the pressure within said expandable member within preselected limits for maintaining the contact pressure between the expandable member and the tissue forming the passage or cavity within preselected limits to minimize the risk of tissue damage, patient discomfort or physiological reflex response, wherein said pressure control includes a pressure responsive fluid regulator coupled to the expandable member for permitting the flow of fluid from the expandable member when the applied pressure on the expandable member increases, regardless of the speed of the pressure increase and for returning fluid to the expandable member when the applied pressure decreases.

11. The combination set forth in claim 10, and including at least one sensor mounted on the catheter and positioned to be placed in pressure engagement with tissue for sensing physiological signals resulting from physiological phenomena, said expandable member being constructed and arranged for maintaining the sensor in pressure engagement with the tissue, said pressure control being coupled to the expandable member for maintaining the contact pressure between the sensor and the tissue within preselected limits to minimize the risk of tissue damage, patient discomfort, physiological reflex response, the exsanguination of blood from beneath the sensor contact area or a likelihood of an introduction of errors into the signal acquired by the sensors.

12. The combination set forth in claims 10, or 11, wherein said pressure control includes a pressure responsive fluid receptor coupled to the expandable member for permitting the flow of fluid from the expandable member when the applied pressure on the expandable member increases and for returning pressurized fluid to the expandable member when the applied pressure decreases.

13. A pressure control system and catheter combination, the combination comprising:

an elongate member for inserting a sensor into a passage or cavity in a human or animal body;

an expandable body mounted on the elongate member and operable to expand to engage tissue forming the margins of the passage or cavity upon being pressurized;

a pressure source coupled to the expandable body and operable to expand said expandable body and;

an elastic-membrane pressure regulator coupled to the expandable body and the pressure source, the elastic-membrane pressure regulator operable to maintain the pressure within the expandable body within preselected limits for indicating, maintaining and/or controlling the contact pressure between the expandable body and the tissue forming the passage or cavity within preselected limits to minimize the risk of tissue damage, patient discomfort, or physiological reflex response, the elastic-membrane pressure regulator operable to expand to permit the flow of fluid from the expandable body when the applied pressure on the expandable body increases, regardless of the speed of the pressure increase, and to contract to permit the return of fluid to the expandable body when the applied pressure decreases.

14. The combination set forth in claim 13, wherein said elastic-membrane pressure regulator includes a rigid-walled chamber with an elastic side-wall portion.

15. The combination set forth in claim 13, wherein said elastic-membrane pressure regulator includes a rigid-walled chamber divided into a first sub-chamber vented to atmosphere and a second sub-chamber by an elastic membrane.

* * * * *